United States Patent [19]

Aburatani et al.

[11] Patent Number: 5,128,464
[45] Date of Patent: Jul. 7, 1992

[54] 6,6-ETHYLENEDIOXY-22R-HYDROXY-2R,3S-ISOPROPYLIDENDIOXY-5α-CHOLST-23-YNE

[75] Inventors: Masakazu Aburatani; Tadashi Takeuchi, both of Toyama; Kenji Mori, Tokyo, all of Japan

[73] Assignee: Fuji Yakuhin Kogyo Kabushiki Kaisha, Toyama, Japan

[21] Appl. No.: 526,527

[22] Filed: May 21, 1990

Related U.S. Application Data

[63] Continuation of Ser. No. 715,252, Mar. 25, 1985, abandoned.

[30] Foreign Application Priority Data

Mar. 30, 1984 [JP] Japan ................... 59-61230

[51] Int. Cl.$^5$ .......... C07J 71/00; C07J 53/00; A61K 31/58
[52] U.S. Cl. ................. 540/16; 552/508; 552/553
[58] Field of Search ............ 540/16; 514/174; 552/508, 553

[56] References Cited

U.S. PATENT DOCUMENTS

| 3,97,687 | 1/1967 | Feldman et al. | 260/239.55 D |
| 3,365,474 | 1/1968 | Fried | 260/239.55 D |
| 3,378,549 | 4/1968 | Edwards et al. | 260/239.55 D |

FOREIGN PATENT DOCUMENTS 0033300  2/1984  Japan ..................... 540/10

OTHER PUBLICATIONS

Sakakibara et al., "Improved Synthesis of Brassinolide", Agrie, Biol. Chem., 47(3), 663–664 (1983).
Sakakibara et al., Heterocycles, 17, 301 (1982).
K. Mori et al., Tetrahedron, 38, 2099 (1982).
Aburatani et al., Agric. Biol. Chem., 49 (12), pp. 3557-3562, (1985).

Primary Examiner—Frederick E. Waddell
Assistant Examiner—T. J. Criares
Attorney, Agent, or Firm—Birch, Stewart, Kolasch & Birch

[57] ABSTRACT

6,6-Ethylenedioxy-22R-hydroxy-2R,3S-isopropylidenedioxy-5α-cholest-23-yne, useful as an intermediate for the synthesis of brassinolide.

1 Claim, No Drawings

6,6-ETHYLENEDIOXY-22R-HYDROXY-2R,3S-ISO-PROPYLIDENDIOXY-5α-CHOLST-23-YNE

This application is a continuation of application Ser. No. 06/715,252 filed on Mar. 25, 1985, now abandoned.

BACKGROUND OF THE INVENTION
1. Field of the invention

The present invention relates to a novel compound, 6,6-ethylenedioxy-22R-hydroxy-2R, 3S-isopropylidenedioxy-5α-cholest-23-yne, useful as a synthetic intermediate for brassinolide.

2. Description of the Prior Art

Brassinolide, (22R,23R,24S)-2α,3α,22,23-tetrahydroxy-24-methyl-B-homo-7-oxa-5α-cholestan-6-one, is a naturally occurring steroid known to have potent plant-growth promoting activity and is expected to present a wide variety of applications in agriculture etc. A number of attempts have been made to develop an efficient process for the synthesis of brassinolide. Processes reported up until now, however, are accompanied, more or less, by certain drawbacks; e.g. use of steroid little found in nature as the starting material and low stereoselectivity, M. J. Thompson et al, Steroids 38 2864-2876 (1981); cumbersome preparation of the side chain, J. B. Siddall et al, J. Am. Chem. Soc. 102 6580-6581 (1980), K. Mori et al, Tetrahedron 38 2099-2109 (1982) and H. Nozaki et al, J. Am. Chem. Soc. 105 4491-4492 (1983); formation of by-products of little use, A. Fiecchi, J. Chem. Soc. Perkin Trans. I 1983 383, M. Anastasia et al, J. Chem. Soc. Perkin Trans. I 1983 2365-2367 and J. Tsuji et al, 45th Yuki-Gosei Symposium (1-7), June 7, 1984; and involvement of many steps, N. Ikekawa et al, J. Chem. Soc. Chem. Comn. 1980, 962-964 and M. Anastasia et al, J. Org. Chem. 49 4297-4300 (1984). Furthermore, the overall yield of brassinolide is quite low in these known processes.

M. Sakakibara and K. Mori reported, in Agric. Biol. Chem., 47 (3) 663-664 (1983), an alternative process for the preparation of brassinolide from stigmasterol abundantly available from natural resources, which is rather simple as compared with other such processes disclosed in the literature mentioned above. The process is reported to involve a step of reacting an aldehyde A with 1,1-dibromo-3-methyl-1-butene and n-butyl lithium to give the acetylene alcohols B1 and B2, as is shown by the following scheme:

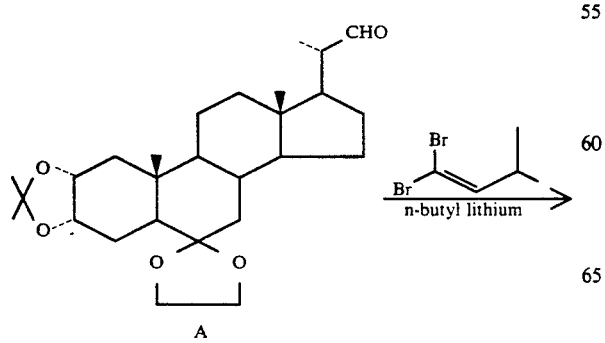

-continued

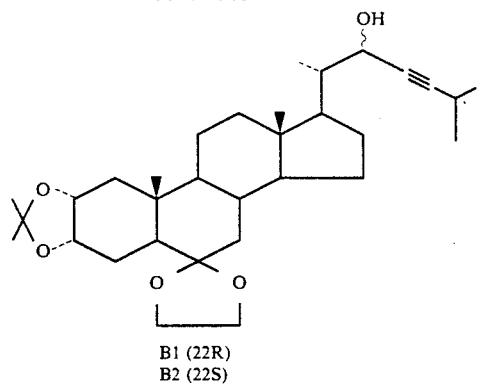

B1 (22R)
B2 (22S)

The aldehyde A is also reported to have been prepared by the method described in the reference cited there, i.e. K. Mori et al, Tetrahedron, 38, 2099 (1982). It is also reported that the overall yield of brassinolide was improved to 3.0% and that the 22S- and 22R-alcohols, B1 and B2, were separable by HPLC.

In following up these alleged results, we have found the following facts:

(1) The starting material for the synthesis of the aldehyde A and, hence the aldehyde A itself, does not have the isopropylidenedioxy residue but the sec-butylidenedioxy residue, and therefore the acetylene alcohols B1 and B2 derived from the aldehyde A are and not of the formula shown above but of the formula (III) and (IV), respectively:

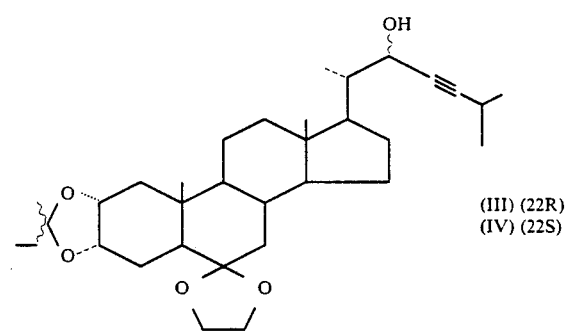

(III) (22R)
(IV) (22S)

(i.e. 6,6-ethylenedioxy-22R (or 22S)-hydroxy-2R, 3S-sec.-butylidenedioxy-5α-cholest-23yne). This will be demonstrated in Referential Example 3 below. It has also been found that the acetylene alcohol III gives two spots in thin layer chromatography (TLC plate: Merck Silica Gel 60F254 Precoat; Eluent: acetone:chloroform = 1:25; Development up to ca. 7 cm followed by coloration with sulfuric acid) and has a molecular weight, as determined by mass spectroscopy, of 528;

(2) A mixture of the acetylene alcohol III and its 22S-isomer IV does not crystallize, which is not desirable from the viewpoint of work-up operations like separation and purification;

(3) The mixture, being a mixture of four isomers, cannot easily be separated even by means of column chromatography.

BRIEF SUMMARY OF THE INVENTION

In accordance with the present invention, there is provided 6,6-ethylenedioxy-22R-hydroxy-2R,3S-isopropylidenedioxy-5α-cholest-23-yne of the formula (I)

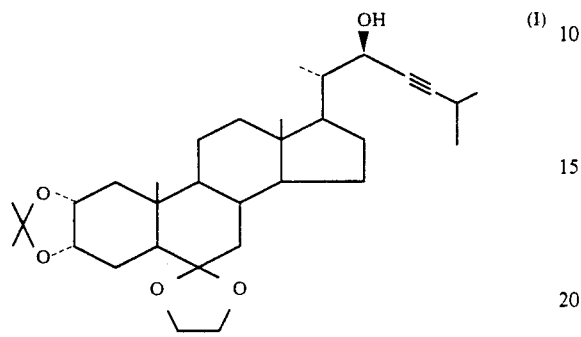

The compound I of the present invention is a novel compound since, as mentioned above, the compound of the same formula shown in Agric. Biol. Chem. 47(3) 663-664 (1983) was found to be a false statement. We have found that the compound I is an extremely useful synthetic intermediate for brassinolide.

The compound I and its 22-S isomer I can be prepared in accordance with a procedure as illustrated by the following Scheme I:

Scheme I

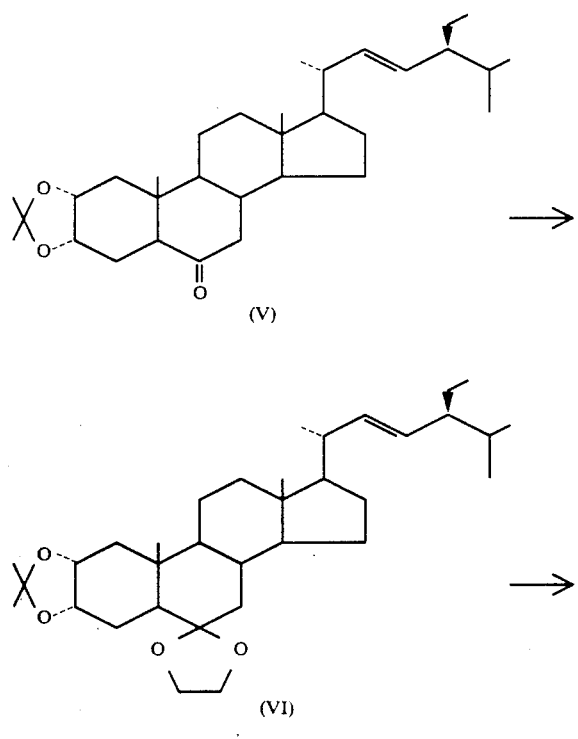

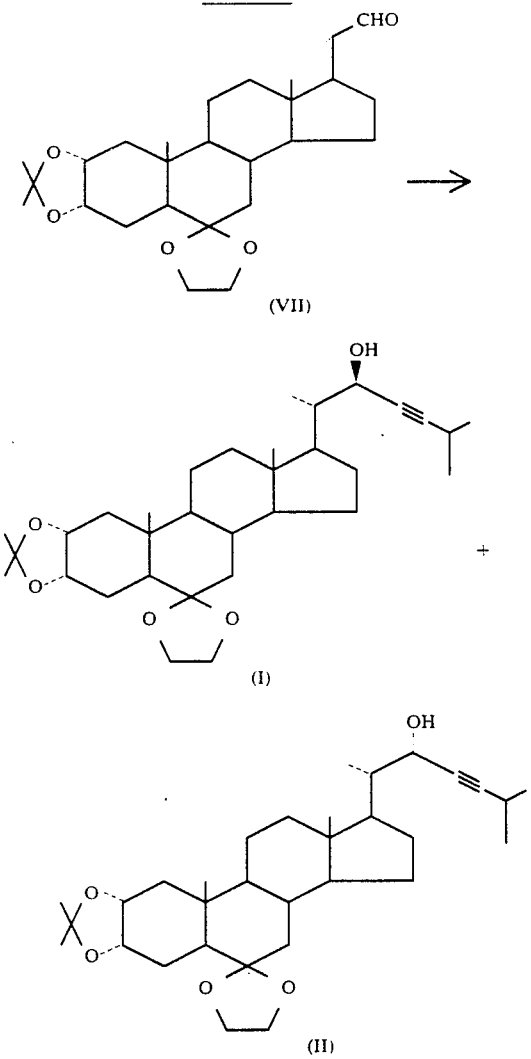

Thus, following Scheme I shown above, an acetonide V, which is a known compound, is used as starting material and converted, by reaction with 2,2-dimethyl-1,3-dioxolan as will be shown in Example 1 below, into a compound VI. The compound VI is converted, by oxidation with ozone, into compound VII, as will be shown in Example 2 below. The compound VII is reacted with 3-methyl-1-butynyl lithium (prepared by 1,1-dibromo-3-methyl-1-butene and n-butyl lithium) to afford the compounds I and II as a mixture (see Example 3). The mixture can be separated into the individual compounds I and II by column chromatography over silica gel using acetone:chloroform (1:20).

We have found that, upon dissolution of a mixture of the compounds I and II in a mixture of a smaller volume of a polar solvent such as toluene, ethyl acetate, chloroform and diethyl ether and a larger volume of a nonpolar solvent such as n-pentane, n-hexane and cyclohexane followed by crystallization with cooling, the compound precipitates as crystals in a selective manner, as will be demonstrated in Example 5 below. Thus, in accordance with the process mentioned above, the compound I can easily be obtained in a simple manner from the mixture I and II without column chromatography which is a cumbersome operation extremely undesirable in large-scale production.

The compound I of the present invention can be converted into its 23S,24R-epoxy derivative, for example in a manner as shown in Referential Example 1. The epoxy derivative can then be converted into brassinolide via castasterone in a conventional manner as described in Agric. Biol. Chem. 47 (3) 663-664 (1983). In the reference, an epoxy derivative is allowed to react with trimethylaluminum and n-butyl lithium in hexane, and the protective groups are then removed.

In contrast with the compound B2 mentioned above, the compound I is a novel crystalline compound with a melting point of 173-175° C. It easily crystallizes and separates, presenting extremely useful and important physical properties as an intermediate for the synthesis of brassinolide.

It has also been found that a mixture rich in the compound II obtainable after removing crystals of the compound I from a mixture of the compounds I and II can be converted, in a good yield, into a mixture rich in the compound I by submitting the first mentioned mixture to oxidation and subsequent reduction (see Example 5) as shown by the following Scheme II:

SCHEME II

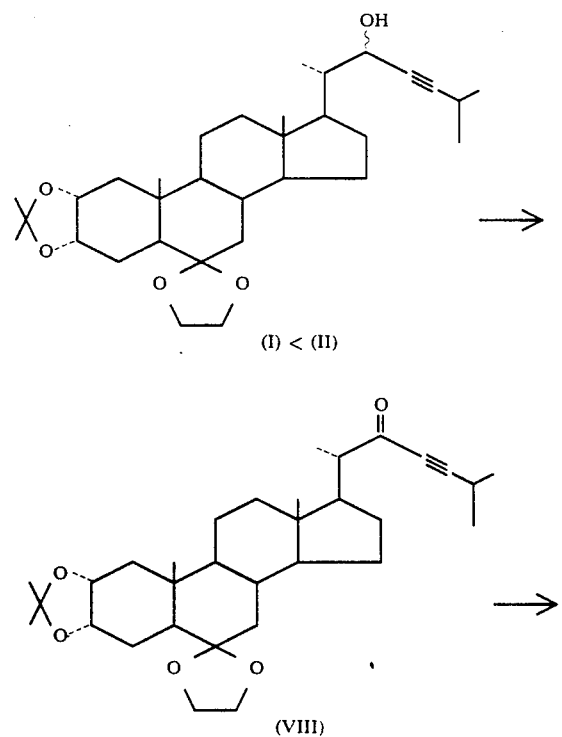

From the thus obtained compound I—rich mixture, the compound I can be selectively crystallized by means of the above mentioned method for crystallization. By repeating this procedure, the compound I can easily be obtained in a good yield from a mixture of the compounds I and II.

As stated above, the compound I easily crystallizes thus rendering separation from its isomer and impurities quite simple and easy. This presents a great advantage, especially in commercial production of brassinolide, over the compounds III and IV which do not crystallize and whose separation is thus only possible by chromatographic operations.

When the compound I is used, in place of the compound 3, in the process as shown in Agric. Biol. Chem., 47 (3) 663-664 (1983), an overall yield of as high as ca. 7% can be reached, a remarkable improvement thus being obtainable. All these results clearly demonstrate remarkable utility of the compound I as an intermediate for the preparation of brassinolide.

DESCRIPTION OF PREFERRED EMBODIMENTS

The preparation of the compound I will now be illustrated in the following examples.

EXAMPLE 1

6,6-Ethylenedioxy-2R,3S-isopropylidenedioxy-24S-ethyl-5α-cholest-22E-ene 500 ml of 2,2-dimethyl-1,3-dioxolane and 1.0 g of p-toluene sulfonic acid were added to 48.5 g (0.1 mole) of the acetonide V, and the mixture was heated under reflux for 3 hours.

After adding 2.0 g of anhydrous potassium carbonate, the reaction mixture was concentrated in vacuo. The residue was purified by chromatography on a silica gel column using ethyl acetate : n-hexane (1:8) as eluent to give 41.5 g of the Ketal VI as an amorphous solid and 4.5 g of the starting material acetonide V. Yield: 78.5% (yield corrected for recovery : 86.5%).

TLC : Rf=0.60 (silica gel, Merck, as specified above.)

Ethyl acetate/hexane=1:3).

$[\alpha]_D^{23b} = +33.7°$ (c=1.03, CHCl$_3$),

EI/MS : m/z 530 (M$^+$ +2, 1.5), 529 (M$^+$ +1, 5.2), 528 (M$^+$, 13.2)

513 (M$^+$ —CH$_3$, 24.6), 317 (100).

EXAMPLE 2

6,6-Ethylenedioxy-2R,3S-isopropylidenedioxy-5α-pregnane-20S-carboxaldehyde 2,000 ml of methylene chloride, 1,000 ml of methanol and 40 g of sodium bicarbonate were added to 40.0 g (0.0756 mole) of the ketal VI, and the solution was cooled to −60° C. Ca. 0.09 mole of ozone was bubbled into the solution over approximately two hours.

After stirring at −50 to −60° C. for 2 hours, gaseous nitrogen was bubbled into the reaction mixture for 30 minutes. 80 ml of dimethyl sulfide was added and the mixture was stirred at −50 to −60° C. for one hour. The reaction mixture was allowed to stand at 0° C. overnight and washed successively with cold 1% hydrochloric acid, 2% aqueous sodium chloride solution and aqueous sodium bicarbonate solution. The methylene chloride solution was dried over anhydrous sodium sulfate and concentrated in vacuo. The concentrate was purified by chromatography on a silica gel column using ethyl acetate : n-hexane (1:6) as eluent to give 30.0 g of the aldehyde VII as a syrup and to recover 2.7 g of the starting material ketal VI. Yield: 85.4% (yield corrected for recovery: 91.5%).

EXAMPLE 3

6,6-Ethylenedioxy-22-hydroxy-2R,3S-isopropylidenedioxy-5α-cholest-23-yne 34.2 g (0.15 mole) of 1,1-dibromo-3-methyl-1-butene was dissolved in 500 ml of tetrahydrofuran and the solution was cooled to −65° C. under an atmosphere of nitrogen. To the solution was added dropwise at −60° to −50° C. 167 ml (0.30 mole) of a 1.8 N solution of n-butyl lithium in hexane.

The solution was then warmed, over one hour, from −60° C. to −40° C., and cooled again to −68° C. To the solution was added dropwise at −65° to −68° C. a solution of 46.5 g (0.10 mole) of the aldehyde VII in 100 ml of tetrahydrofuran.

The resulting mixture was stirred for one hour and then allowed to warm up to 0° C. over a period of 2 hours. After adding 50 ml of a saturated aqueous ammonium chloride solution, water and ether, the phases were separated.

The ether layer was washed with a saturated aqueous sodium chloride solution, dried over anhydrous sodium sulfate and concentrated in vacuo to give 53.0 g of the crude acetylene alcohols (I+II). 20 g of the products was purified by chromatography on a column packed with 200 g of silica gel using ethyl acetate : n-hexane (1:4) to give 17.55 g of the pure acetylene alcohols (I+II) as a syrup. Yield 90.3%. I/I+II = 53%.

EXAMPLE 4

6,6-Ethylenedioxy-22R-hydroxy-2R,3S-isopropylidenedioxy-5α-cholest-23-yne 20 g of the crude acetylene alcohols (I+II) obtained in Example 3 was dissolved at 50° C. in 4.0 ml of toluene and 100 ml of n-hexane. The solution was cooled to 15° C. and 0.1 g of compound I in crystalline form was then added thereto. The mixture was stirred at 10°-12° C. for 48 hours. The crystals formed were filtered off to obtain 6.0 of a product. The product was added to 1.2 ml of ethyl acetate and 12 ml of hexane and the resulting mixture was stirred at 50° C. for 30 minutes and then allowed to stand at 0° C. overnight.

The crystals formed were filtered off to obtain 5.03 g of a product, m.p. 172°-175° C. The product was found, by means of a TLC scanner, to be the compounds I+II with I/I+II of 98.7%.

15.0 g of the pure acetylene alcohols (I+II) obtained in Example 3 was dissolved at 50° C. in 3.0 ml of ethyl acetate and 60 ml of n-hexane, and the solution was stirred at 10°-12° C. for 48 hours.

The crystals formed were filtered off and dried to give 5.85 g of a product. The product was suspended and purified as in 1) above to give 4.90 g of compound I, m.p. 173°-175° C. I/I+II = 99.3%.

EI/MS : m/z 515 (M$^+$+1, 6.8), 514 (M$^+$, 18.0), 500 (M$^+$ −CH$_3$+, 19.4), 499 (M$^+$ −CH$_3$, 55.6), 303 (100).
[cf. Data for compound III:
EI/MS : m/z 529 (M$^+$+1, 0.5), 528 (M$^+$, 0.8), 515 (M$^+$ −CH$_3$+2, 2.0), 514 (M$^+$ −CH$_3$+1, 6.1), 513 (M$^+$ −CH$_3$, 17.8), 501 (M$^+$ −C$_2$H$_5$+2, 7.6), 500 (M$^+$ −C$_2$H$_5$+1, 35.8), 499 (M$^+$ −C$_2$H$_5$, 100).]

EXAMPLE 5

6,6-Ethylenedioxy-22-hydroxy-2R,3S-isopropylidenedioxy-5α-cholest-23-yne 1) 26.8 g (0.052 mole) of the acetylene alcohols I and II (I/I+II=29.6%), obtained by concentrating the mother liquor after filtering off the crystals in Example 4,2), was dissolved in 130 ml of toluene and 65 ml of dimethylsulfoxide and the solution was cooled to 5° C. 2.08 ml (0.026 mole) of pyridine, 1.04 ml (0.013 mole) of trifluoroacetic acid and 16.1 g (0.078 mole) of N,N-dicyclohexylcarbodiimide were successively added to the solution. The reaction mixture was stirred at 10 -15° C. for 20 hours. After adding 360 ml of toluene, the mixture was filtered. the filtrate was washed three times with 260 ml portions of water. The organic layer was dried over anhydrous sodium sulfate and then concentrated in vacuo to give compound VIII.

260 ml of methanol was added to the product, and 1.0 g (0.026 mole) of sodium borohydride was added to the mixture with cooling and stirring at 5° C. After 30 minutes an additional 1 g of sodium borohydride was added and the mixture was stirred at 10°-15° C. for 2 hours. The reaction mixture was concentrated in vacuo, diluted with 520 ml of toluene and washed three times with 130 ml portions of water.

The toluene layer was dried over anhydrous sodium sulfate and concentrated in vacuo. The concentrate was purified by chromatography on a column packed with 300 g of silica gel using ethyl acetate : n-hexane (1:4) as eluent to give 22.06 g of the acetylene alcohols (I/I+II=63.1%). Yield: 82.3%.

The product was dissolved in 2.2 ml of ethyl acetate and 110 ml of n-hexane, and the solution was stirred at 5°-10° C. for 24 hours. The crystals formed were filtered off. Yield: 10.10 g (I/I+II=92.4%).

2) 30.9 g (0.06 mole) of the acetylene alcohols (I/I+II=27.3%), obtained from another reaction system in the same manner as in 1) above, was dissolved in 600 ml of ethyl acetate, and the solution was cooled to 0° C. While vigorously stirring, 18.0 ml of Jones reagent (a solution of 4.8 g chromium trioxide in dilute sulfuric acid) was added dropwise to the solution over a period of 30 minutes. After a further 30 minutes of stirring, 60 ml of water was added and the phases were separated. The organic layer was washed successively with water, a saturated aqueous sodium bicarbonate solution and a standard aqueous sodium chloride solution.

The layer was dried over anhydrous sodium sulfate, treated with activated carbon and concentrated in vacuo to dryness to give compound VIII. The product was dissolved in 600 ml of toluene and cooled to −65° C. To the solution was added dropwise 17.3 g (0.06 mole) of a 70% solution of sodium bis(2-methoxyethoxy)aluminum hydride in toluene over 30 minutes. After stirring at 31 65° to −60° C. for 2 hours, 20 ml of methanol was added dropwise to the mixture.

After being allowed to warm up to 0° C., the mixture was mixed with 120 ml of water and filtered to remove insolubles. The filtrate was phase-separated and the organic layer was washed with water dried over anhydrous sodium sulfate, treated with activated carbon and concentrated in vacuo to dryness to give 28.7 g of the acetylene alcohols (I/I+II=82.4%). 6 ml of ethyl acetate and 60 ml of n-hexane were added to the product.

After stirring at 50° C. for 30 minutes, the mixture was stirred at 10°–12° C. for 20 hours. The crystals formed were filtered off and dried to give 18.1 g of the acetylene alcohol I (I/I+II=98.8%).

REFERENTIAL EXAMPLE 1

23S,24R-Epoxy-6,6-ethylenedioxy-22R-hydroxy-2R,3S-isopropylidenedioxy-5α-cholestane 2.49 g (0.01 mole) of nickel acetate was dissolved in 50 ml of ethanol. 20 ml of a 1M solution of sodium borohydride in ethanol was added to the solution with stirring. After 1.34 ml (0.02 mole) of ethylenediamine was added, 20.6 g (0.04 mole) of the acetylene alcohol I and 200 ml of ethanol were added. After establishing an atmosphere of hydrogen in the reaction system, the mixture was catalytically reduced with stirring. After 5 hours of stirring, 300 ml of ether and 5 g of Hyflo Super Cel were added and the mixture was filtered.

The filtrate was concentrated in vacuo, mixed with 500 ml of ether and washed three times with water.

The organic layer was dried over anhydrous sodium sulfate and concentrated in vacuo to give 22.5 g of a caramel-like solid. The product was dissolved in 1,200 ml of methylene chloride, mixed with 20 g of anhydrous sodium monohydrogen phosphate in powder form and 20.7 g of m-chloroperbenzoic acid (purity 88.3%) and stirred at 5°–10° C. for 20 hours.

The reaction solution was poured into 600 ml of a 0.05 N aqueous caustic soda solution and the phases were separated. The organic layer was washed with water and an aqueous sodium chloride solution, dried over anhydrous sodium sulfate and concentrated in vacuo. The concentrate was purified by chromatography on a silica gel column using ethyl acetate : n-hexane=1.3 to give 20.12 g of the title epoxide as white crystals.

Yield 94.4%. M.P. 181°–182° C.

EI/MS : m/z 533 (M$^+$+1, 3.0), 532 (M$^+$, 8.9), 518 (M$^+$—CH$_3$—1, 12.3), 517 (M$^+$—CH$_3$, 33.7), 321 (100).

REFERENTIAL EXAMPLE 2

Castasterone 16.0 g of 23S,24R-epoxy-6,6-ethylenedioxy-22R-hydroxy-2R, 3S-isopropylidenedioxy-5α-cholestane was dissolved in 1.6 l of n-hexane and 0.4 l of cyclohexane.

After establishing a nitrogen atmosphere in the reaction system, the solution was cooled to −70° C. 100 ml of a 15% solution of trimethylaluminum in hexane and 10 ml of a 15% solution of n-butyl lithium in hexane. The mixture was stirred at −70° C. for one hour and then allowed, with stirring, to warm up to +10° C. over a 4 hours. It was then cooled to −40° C. and 1.6 l of 1N hydrochloric acid was added to decompose the trimethylaluminum. The mixture was extracted with ethyl acetate. The organic layer was washed with water, dried over anhydrous sodium sulfate and concentrated in vacuo. 200 ml of 80% acetic acid was added to the concentrate and the mixture was stirred at 50–60° C. for one hour. It was then neutralized with sodium carbonate and extracted with ethyl acetate. The ethyl acetate layer was washed with water, dried over anhydrous sodium sulfate and concentrated in vacuo. The residue was purified by column chromatography on 800 g of silica gel using methanol/chloroform 1/25–1/10 to give 7.62 g of crystalline castasterone. Re-crystallization from ethyl acetate +methanol gives the product with a melting point of 256°–259° C.

REFERENTIAL EXAMPLE 3

6,6-Ethylenedioxy-2R,3S-sec.butylidenedioxy-24S-ethyl-5α-cholest-22E-ene (VIb+VIb′)

10 ml of 2-methyl-2-ethyl-1,3-dioxolane and 0.1 g of p-toluenesulfonic acid were added to 2.0 g of the acetonide V and the mixture was heated under reflux for 3 hours. 0.5 g of anhydrous potassium carbonate was added to the reaction mixture and the mixture was stirred for 10 minutes. After adding ether, it was filtered to remove insolubles. The filtrate was washed with a saturated aqueous solution of sodium bicarbonate, dried over anhydrous potassium carbonate and concentrated in vacuo. The resulting reaction products were separated and purified by chromatography on a silica gel column using acetone : n-hexane (1:20) as eluent to give 1.08 g of compound VIb and 0.92 g of compound VIb′. 6,6-ethylenedioxy-2R,3S-sec-butylidenedioxy-24S-ethyl-5α-cholest-22E-ene gives two spots in thin layer chromatography (Merck silica gel 60F254 precoat; ethyl acetate/n-hexane=1/3).

Compound VIb :

Rf : 0.71 (Ethyl acetate : n-hexane=1:3);
$[\alpha]_D^{23}$ = +34 8° (c=1.05, CHCl$_3$);
EI/MS: m/z 542 (M$^+$, 0.3) 541 (M$^+$−1, 0.5), 528 (M$^+$+1—CH$_3$, 0.4), 527 (M$^+$—CH$_3$, 1.0), 526 (M$^+$−1—CH$_3$, 2.5), 513 (M$^+$—C$_2$H$_5$, 38), 512 (M$^+$−1—C$_2$H$_5$, 100).

Compound VIb′:

Rf : 0.64 (Ethyl acetate : n-hexane=1:3);
$[\alpha]_D^{23}$ = +34.7° (c=1.03, CHCl$_3$);
EI/MS : m/z 542 (M$^+$, 1.7), 541 (M$^+$−1, 4.1), 528 (M$^+$+1—CH$_3$, 5.3), 527 (M$^+$—CH$_3$, 15.9), 526 (M$^+$−1 —CH$_3$, 41.6), 513 (M$^+$ —C$_2$H$_5$, 36.5), 512 (M$^+$−1—C$_2$H$_5$, 100).

Compounds VI, VIb and VIb′ showed much the same 200 MHz NMR pattern for δ values between 2.7 and 5.3.

TLC with the reaction solution obtained by adding 1.0 ml of 2-methyl-2-ethyl-1,3-dioxolane and 0.01 g of p-toluenesulfonic acid to 0.1 g of the ketal VI and heating the mixture under reflux for 3 hours was identical to that with compound VIb + compound VIb′.

These results can be schematically shown as follows:

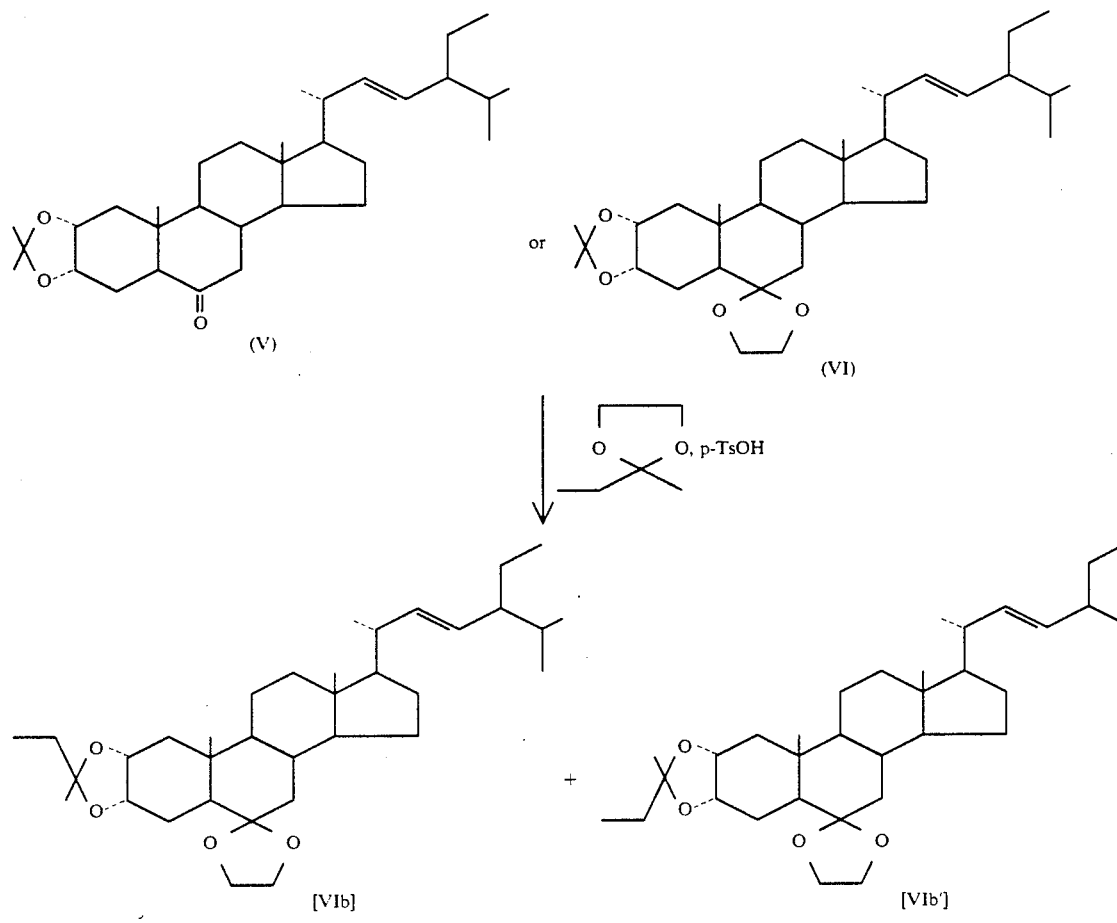
This clearly demonstrates that the product "7c" actually obtained in K. Mori et al, Tetrahedron, 38, 2099 (1982) was not "6,6-Ethylenedioxy-2α,3α-isopropylidenedioxy-24S-ethyl-5α-cholest-22E-ene" but a mixture of two isomers of 6,6-ethylene-dioxy-2R, 3S-sec-butylidenedioxy-24S-ethyl-5α-cholest-22E-ene.
What is claimed is:
1. 6,6-Ethylenedioxy-22R-hydroxy-2R,3S-isopropylidenedioxy-5α-cholest-23yne of the formula:
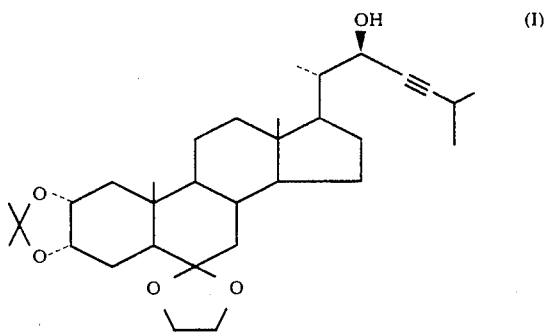
* * * * *

UNITED STATES PATENT AND TRADEMARK OFFICE
CERTIFICATE OF CORRECTION

PATENT NO. : 5,128,464

DATED : July 7, 1992

INVENTOR(S) : Masakazu Aburatani; Tadashi Takeuchi and Kenji Mori

It is certified that error appears in the above-identified patent and that said Letters Patent is hereby corrected as shown below:

Title page, item [54] and col. 1, in the title, change "ISOPROPYLIDENDIOXY" to --ISOPROPYLIDENEDIOXY-- and line 3, change "CHOLST" to --CHOLEST--

Column 1, Line 2, change "PROPYLIDENDIOXY" to --PROPYLIDENEDIOXY-- and change "CHOLST" to --CHOLEST--.

Signed and Sealed this

Fourteenth Day of September, 1993

*Attest:*

BRUCE LEHMAN

*Attesting Officer*      Commissioner of Patents and Trademarks